United States Patent
Frank (10) Patent No.: US 9,841,409 B2
(45) Date of Patent: Dec. 12, 2017

(54) BALANCED FEATURE DISPLAY IN FLUIDIC SAMPLE SEPARATION

(75) Inventor: Michael Frank, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 1002 days.

(21) Appl. No.: 13/423,863

(22) Filed: Mar. 19, 2012

(65) Prior Publication Data

US 2012/0265448 A1 Oct. 18, 2012

(30) Foreign Application Priority Data

Apr. 18, 2011 (GB) .................................. 1106493.8

(51) Int. Cl.
 *G09F 19/00* (2006.01)
 *G01N 30/86* (2006.01)

(52) U.S. Cl.
 CPC .................. *G01N 30/8651* (2013.01)

(58) Field of Classification Search
 CPC ....... G01N 2201/1293; G01N 30/8631; G01N 30/8624; G01N 30/8675; G01N 30/8679; G01N 30/8651; G06F 19/00
 USPC ............................................ 702/22, 25, 32
 See application file for complete search history.

(56) References Cited

U.S. PATENT DOCUMENTS

| | | | |
|---|---|---|---|
| 6,748,333 B1* | 6/2004 | Ito | G01N 30/8624 702/195 |
| 2005/0206644 A1* | 9/2005 | Kincaid | G06T 11/206 345/440 |
| 2005/0251349 A1* | 11/2005 | Ito et al. | 702/22 |
| 2006/0281993 A1* | 12/2006 | Pedrizzetti | A61B 8/0858 600/443 |

(Continued)

FOREIGN PATENT DOCUMENTS

| | | |
|---|---|---|
| DE | 102007000627 A1 | 5/2009 |
| GB | 2383963 A | 7/2003 |

(Continued)

OTHER PUBLICATIONS

Neils Bindslev, Drug-Acceptor Interactions Modeling Theoretical Tools to Test and Evaluate Experimental Equilibrium Effects, Co-Action Publishing, 2008, chapter 9, pp. 233-255.*

(Continued)

*Primary Examiner* — Janet Suglo
*Assistant Examiner* — Lisa Peters (57) ABSTRACT

A device for processing measurement data assigned to a measurement on a fluidic sample to be separated, the measurement data having multiple features being indicative of different fractions of the fluidic sample, the device includes a feature position analysis unit configured for analyzing positions ($p_1$, $p_2$, $d_1$, $d_2$) of at least a part of the features relative to one another, and a display adjustment unit configured for adjusting, based on a result of the analyzing, a mode of displaying at least a part of the features along at (Continued)

least one display axis of a display diagram so that at least a part of adjacent features is positioned equidistantly along the at least one display axis or so that at least a part of adjacent features is positioned to have a distance (d) from one another which is larger than or equal to a predefined threshold value ($d_{th}$).

19 Claims, 8 Drawing Sheets

(56) References Cited

U.S. PATENT DOCUMENTS

2008/0201085 A1* 8/2008 Pauli et al. .................. 702/25

FOREIGN PATENT DOCUMENTS

| JP | 2-044249 A | 2/1990 |
| JP | 5-048467 A | 2/1993 |
| JP | 2000-131304 A | 5/2000 |
| JP | 2000131304 A | 5/2000 |
| JP | 2008-101960 A | 5/2008 |
| JP | 2008101960 A | 5/2008 |

OTHER PUBLICATIONS

Search Report dated Jul. 25, 2011, by the United Kingdom Intellectual Property Office with regard to related Application No. GB1106493.8 (4 pages).
Office action dated Dec. 2, 2015 from U.K. Patent Application No. GB1106493.8.

* cited by examiner

BALANCED FEATURE DISPLAY IN FLUIDIC SAMPLE SEPARATION

BACKGROUND ART

The present invention relates to a data analysis system.

Measurement instruments are applied to execute various measurement tasks in order to measure any kind of physical parameter. As a result of a measurement, measurement data is output by the measurement instrument. Such measurement data may include values of physical parameters such as concentrations of components of a sample, intensity values of a fluorescence measurement, etc., in dependency of another parameter such as a chromatographic retention time. This information can be displayed to a user via a graphical user interface for evaluation of the data.

An example for such a measurement instrument is a coupled liquid chromatography and mass spectroscopy device (for instance the 1200 Series LC/MSD of Agilent Technologies).

DE 10 2007 000 627 A1 discloses a device which has a processing unit, for instance a CPU, for processing of measured data of a liquid chromatography measurement and mass spectrometer measurements such that the processed data are represented in two-dimensions. Parameters such as retention time and mass spectrometer-spectrum characterizing the measurements are represented in dimensions, where the latter parameter is correlated with the former parameter. The processing unit is arranged such that data of an original sample, i.e. fluid sample, and data of fragments of the sample are represented in two dimensions.

For the management of measurement data, a user interface may be required for displaying measurement results to a user in a technically intuitive manner.

DISCLOSURE

It is an object of the invention to provide a data analysis system capable of preprocessing measurement data to simplify subsequent interpretation by a user.

According to an exemplary embodiment, a device for processing measurement data assigned to a measurement on a fluidic sample to be separated is provided, the measurement data having multiple features being indicative of different fractions of the fluidic sample, the device comprising a feature position analysis unit configured for analyzing positions of at least a part of the features (particularly feature positions in the measurement data) relative to one another (i.e., at least a subset of the features), and a display adjustment unit configured for adjusting, based on a result of the analyzing, a mode of displaying at least a part of the features along at least one display axis of a display diagram so that at least a part of adjacent features (particularly features being located non-equidistantly in the original measurement data) is positioned equidistantly along the at least one display axis, or so that at least a part of adjacent features (particularly features having a distance from one another which is smaller than a predefined threshold value in the original measurement data, for instance overlapping features) is positioned to have a distance from one another which is larger than or equal to a predefined threshold value (for instance to remove overlap of adjacent features).

According to another exemplary embodiment, a method of processing measurement data assigned to a measurement on a fluidic sample to be separated is provided, the measurement data having multiple features being indicative of different fractions of the fluidic sample, wherein the method comprises analyzing positions of at least a part of the features (i.e., at least a subset of the features) relative to one another, and adjusting, based on a result of the analyzing, a mode of displaying at least a part of the features along at least one display axis of a display diagram so that at least a part of adjacent features is positioned equidistantly along the at least one display axis, or so that at least a part of adjacent features is positioned to have a distance from one another which is larger than or equal to a predefined threshold value.

According to still another exemplary embodiment of the present invention, a software program or product is provided, preferably stored on a data carrier, for controlling or executing the method having the above mentioned features, when run on a data processing system such as a computer.

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of measurement data analysis. The measurement data analysis scheme according to an embodiment of the invention can be performed or assisted by a computer program, i.e. by software, or by using one or more special electronic optimization circuits, i.e. in hardware, or in hybrid form, i.e. by means of software components and hardware components.

In the context of this application, the term "measurement data" (or measurement signal) may particularly denote experimental data obtained from a measurement regarding a sample comprising multiple fractions or components which are to be separated from one another. For example, such measurement data may be liquid or gaseous chromatography data.

The term "feature" (more particularly signal feature) may particularly denote a characteristic subsection in a measurement signal which has a special shape, value, etc., which distinguishes the subsection from surrounding portions. When referring to a "signal feature", "signal " should be understood as relating to a measurement signal of any type such as a chromatogram. For example, such a feature may be a peak, a dip, a step or the like in the signal with a dedicated pattern being indicative of a certain measurement event.

The term "fractions of a fluidic sample" may particularly denote different components (such as different chemical or biological compounds) of a fluidic sample, i.e. of a gaseous and/or liquid sample. For example, different genes or different proteins in a biological sample can form the different fractions. By a fluid separation method performed by the measurement device, it is possible to physically and spatially separate the different fractions of the fluidic sample, for instance by liquid or gaseous chromatography or gel electrophoresis.

The term "analyzing positions of features relative to one another" may particularly denote that individual positions of the features in a signal or measurement spectrum and/or distances between adjacent features in a signal or measurement spectrum are determined. Correspondingly determined characteristics of the positional distribution may then be analyzed. Particularly, this may include determining pairwise distances between consecutive features, for instance between successive local maxima of peaks. If desired, position analysis may be performed in combination with one or more other characteristic parameters such as a full width half maximum and/or a symmetry, a peak form (Gaussian, Lorentzian, Voigtian, etc.). This analysis may be performed with the aim to derive characteristic information usable for setting up a display of the features in a non-overlapping way thereby facilitating interpretation of the features for a user.

The term "mode of displaying" may particularly denote a style according to which the signal including the features is plotted for instance in a diagram. A standard mode of displaying which is conventionally used is a linear or a logarithmic scale, wherein the signal is plotted along an axis of a diagram in accordance with such a scale function. However, an adjustment of the mode of display according to exemplary embodiments may include a coordinate transformation or other kind of manipulation either for the complete measurement data or individually for different sections of the measurement data, so as to derive a non-linear or non-monotonic plotting characteristic.

The term "display axis of a display diagram" may particularly denote an abscissa or an ordinate or any other coordinate axis along which a parameter of the measurement data is plotted in a corresponding coordinate system.

The term "adjacent features" may particularly denote features in the measurement signal or measurement data which features are directly neighbored, i.e. are located next to one another without any other identified feature in between. Hence, each two consecutive features may form a pair of adjacent features. To allow a user to interpret individual features separately, the adjacent features should be visually distinguishable in a display diagram. Hence, the mode of displaying may be adjusted so that adjacent features are visually separable.

The term "positioned equidistantly" may particularly denote that the corresponding features are plotted along the display diagram so that the physical plotting distance between two directly neighbored features is the same for all adjacent feature pairs of the equidistantly plotted section.

The term "predefined threshold value" may particularly denote a value indicating a minimum distance between adjacent features in a manipulated plot. This value may be fixedly defined, for instance in a database, or may be defined by a user in accordance with user preferences. For instance, the predefined threshold value may be quantified in accordance with expert knowledge or theoretical or empirical data. It may be selected so that an overlap between displayed features can be overcome.

The term "value of a measurement parameter" may particularly denote a quantitative value of a measured parameter in a certain measurement. Which measurement parameter is analyzed depends on the kind of measurement being performed.

According to an exemplary embodiment, a system for illustrating sections of measurement data relating to individual components of a fluidic sample to be separated by a sample separation method is provided which visualizes the individual features of a corresponding measurement signal in a technically meaningful manner thereby simplifying it for a user to interpret the measurement results correctly. For this purpose, a (for instance normally linear) display axis (such as a retention time axis of a chromatogram) may be rescaled in such a manner that the peaks or other features are plotted equidistantly or are plotted at least with a predefined distance from one another.

In other words, in one embodiment or configuration, at least a portion of the measurement signal may be rescaled for display so that the distance between each pair of adjacent features in the displayed diagram is the same for a plurality of pairs, which pairs do not have the same distance in the original measurement data before manipulation.

In an alternative, at least a part of the measurement signal may be rescaled for display so that the distance between each pair of adjacent features in the displayed diagram is not less than the predetermined threshold value for a plurality of pairs, which pairs do not all have a sufficiently large distance in the original measurement data before manipulation. Pairs which have a sufficiently large distance in the original measurement data before manipulation may be plotted with their original distance which may differ from the predetermined threshold value.

For this purpose, the measurement data is analyzed first with regard to a positional characteristic of the features relative to one another. Subsequently, at least one display axis may be manipulated in accordance with the previously performed positional characteristic analysis in such a manner that the features in the displayed diagram have at least a certain minimum distance from one another or are at least more evenly distributed along the entire axis. This may result in a non-constant density according to which the respective measurement parameter is plotted along the respective display axis. By taking this measure, the distance between the plotted features may be made sufficiently large so as to enable a meaningful interpretation of the features and therefore of the measurement result. This makes the identification of the features more reliable and provides a regular pattern of displayed features which has turned out to be particularly intuitive for the human eye for interpreting the features.

More generally, the display manipulation unit may be configured for manipulating a mode of displaying at least a part of the identified features along at least one display axis of the display diagram so that display of at least a part of the identified features is more evenly distributed along the at least one display axis as compared to a linear display of these features along the at least one display axis under consideration of the boundary condition that adjacent features in the manipulated display have a distance exceeding a predefined threshold value.

In the following, further exemplary embodiments of the device will be explained. However, these embodiments also apply to the method and to the software program or product.

In an embodiment, the display adjustment unit is configured for adjusting the mode of displaying so that all features are located equidistantly along the at least one display axis. Alternatively, all adjacent features may be positioned to have a distance from one another which is larger than or equal to the predefined threshold value. Thus, a visually separable appearance of the individual features can be ensured over the entire range of the measurement signal.

In an embodiment, the display adjustment unit is configured for adjusting the mode of displaying so that a part of the features is compressed along a corresponding portion of the at least one display axis and another part of the features is expanded along a corresponding other portion of the at least one display axis. A display density function may hence comprise a characteristic with alternating regions of sections with a display density above an average value and of sections with a display density below the average value. High density sections may relate to regions of the measurement signal with a relatively small number of features, whereas low density sections relate to a portion of the spectrum with a relatively high amount of features to be displayed. Thus, individual sections of the measurement signal may be manipulated separately and differently.

In an embodiment, the display adjustment unit is configured for adjusting the mode of displaying so that at least a part of adjacent features is positioned to have a distance from one another which is below a further predefined threshold value. According to this embodiment, not only the minimum distance between directly neighbored features is regulated but also their maximum distance. Hence, regions requiring a lot of display space without showing a large number of features can be Limited with regard to their consumed display space to use the latter more efficiently.

In an embodiment, the display adjustment unit is configured for determining a density function to be displayed along the at least one display axis indicative of a varying density according to which a parameter is displayed along the at least one display axis in the adjusted mode. By not only plotting the features along an axis, but by simultaneously plotting the density function, a user can recognize with a single view which portions of the measurement spectrum are compressed (high value of the density function) and which portions are expanded (relatively small value of the density function). Therefore, the impact of the manipulation is easily visible for a user, thereby safely preventing false interpretation in view of the manipulation. Preferably, the density function is plotted parallel to the plotting of the corresponding parameter, thereby allowing an easy visual correlation.

In an embodiment, the density function may be displayed by a color encoded display of the density function, a display of the density function in terms of scaling markers arranged along the at least one display axis and/or a density function coordinate system displaying a curve indicative of the density function. A color encoded display of the density function may be a bar in which a color code is indicative of a value of the density function. For instance, light gray portions in such a color encoded display may indicate small density values, dark gray values may indicate higher densities. Additionally or alternatively, the density function may be plotted via scaling markers, i.e. markers along an axis optionally provided with numbers indicating distances between adjacent markers to a user. For instance, adjacent scaling markers may relate to the same real distance of the parameter, so that a physical distance of the plotted scaling markers gives an indication for the density function. Plotting the density function in a coordinate system is another way of intuitively visualizing the density function a user.

In an embodiment, the adjusted mode of displaying at least the part of the features is a mode of displaying them in accordance with a polynomial density function along the at least one display axis of the display diagram. A polynomial function is a function that can be defined by evaluating a polynomial. A polynomial function is a continuous function which can also be fitted with a reasonable number of parameters and thus low computational burden on the basis of the identified positional relationship between the individual features.

In an embodiment, the adjusted mode of displaying at least the part of the features is a mode of displaying exclusively an excerpt of the measurement data between a first defined feature and a last defined feature in an ordered representation along the display axis. In such an embodiment, it is also possible that only a portion of the measurement data or measurement signal is plotted and manipulated. Such an excerpt may be a portion of the measurement signal which nevertheless includes all features, thereby disregarding measurement portions without identified features. Therefore, the entire display may be concentrated on the technically meaningful part of the measurement signal. Hence, the first defined feature relates to the feature at the lowest value of the parameter plotted along the display axis, whereas the last defined feature relates to the feature with the largest value of the measurement parameter.

In an embodiment, each feature represents a combination of a value of a first measurement parameter with a value of a second measurement parameter, wherein the display diagram is a coordinate system having a first display axis along which the value of the first measurement parameter is displayable for at least a part of the features in accordance with the adjusted mode of displaying and having a second display axis along which the value of the second measurement parameter is displayable for at least a part of the features, particularly in accordance with a linear mode of displaying. For example, the first measurement parameter may be the retention time of a liquid chromatography experiment, whereas the second measurement parameter may be an intensity (such as an absorption intensity) of the measurement (chromatogram). In such an embodiment, the first measurement parameter such as the retention time is plotted in the manipulated manner, whereas the intensity or other second measurement parameter is plotted along an ordinate in a linear manner.

In an alternative embodiment, each feature represents a combination of a value of a first measurement parameter with a value of a second measurement parameter, wherein the display diagram is a coordinate system having a first display axis along which the value of the first measurement parameter is displayable for at least a part of the features in accordance with the adjusted mode of displaying, wherein the value of the second measurement parameter is displayable for at least a part of the features encoded by a graphical property of a respective marker in the coordinate system. This embodiment allows to plot the second parameter (such as the absorption intensity of a chromatographic spectrum) encoded as a graphical property, so that for instance each feature is represented by a circle or other graphical property with the individual graphical properties being plotted along the display axis in the manipulated way. Such a bubble plot allows to display the information with a small area demand.

In an embodiment, the graphical property is a size of the marker, particularly an area of a circular marker. For example, the larger the value of the second measurement value, the larger the area of the marker. Hence, the area of such a marker can be used as an indication of how pronounced the feature is in the original measurement signal, for instance which area a corresponding peak of a liquid or gaseous chromatography measurement has. However, it is also possible to use additionally or alternatively indicators other than the size of the marker—for instance a color—for indicating the value of the second measurement parameter. Encoding the value of the second parameter in the graphical property is a very intuitive way of indicating the value of a second parameter to a user.

Still referring to the previously described embodiment, the measurement data has a plurality of data sets, each data set being assigned to a respective one of a plurality of measurements, each data set having multiple features being indicative of different fractions of a fluidic sample, wherein the display diagram has a second display axis along which at least a part of the data sets is displayable for at least a part of the features. The term "data set" may particularly denote a portion of the measurement data, more precisely experimental data which relate to one and the same measurement on one and the same fluidic sample. For instance, multiple measurements may be performed with multiple physically different samples, whereas the samples are preferably treated under same or comparable measurement conditions. Hence, each data set may correspond to a respective one of several experimental runs on a measurement device for separating a corresponding fluidic sample in the different fractions. It is possible to use different samples, one for each measurement relating to a corresponding data set. In another embodiment, it is possible to use the same sample and run the same experiment multiple times to capture various data sets together forming the measurement data. By encoding the value of the second measurement parameter in a two-dimensional representation via the graphical property, it is possible to plot the different measurements along the second coordinate axis. The manipulation or density function may be the same for each of the data sets, so that the individual measurements plotted one above the other allows for an easy correlation of corresponding features for a user.

In an embodiment, the coordinate system is a Cartesian coordinate system. Alternatively, other two dimensional coordinate systems are possible. Also a three- or more-dimensional coordinate system may be used. However, the use of a Cartesian coordinate system makes the visual understanding of the feature distribution by a user very easy, since the display manipulation can be easily derived visually from a Cartesian coordinate system.

In an embodiment, the first parameter is indicative of a retention time (or a retention volume) of a chromatography measurement, or a mass to charge ratio of a coupled liquid chromatography and mass spectroscopy measurement. However, these parameters are only exemplary, since other parameters may be used when other kinds of measurements are carried out.

In an embodiment, the second parameter is indicative of a detection intensity of a peak of a chromatography measurement. Again, also the second parameter may be different from the detection intensity when other measurements are carried out.

In an embodiment, the feature position analysis unit is configured for analyzing positional distances between at least a part of adjacent features. In this embodiment, the feature position analysis unit calculates the distance between features of each pair of directly neighbored features in the original measurement data, i.e. before manipulation. On the basis of the determined distances, the distances may be either accepted for non-manipulated display if they are not too large and/or not too small. If the distance is considered to be too large or too small, then there are two possibilities. The first possibility is that the manipulated distance is adjusted to be at least the predetermined threshold value. Another strategy is to arrange all features in an equidistant way along the measurement axis. The calculation of the corresponding density function can then be performed so that, upon applying the density function to the determined positions, the resulting manipulated representation meets the requirements of an equidistant arrangement or of an arrangement with a distance of at least the predetermined threshold value.

In an embodiment, the feature position analysis unit is configured for analyzing positions of only a part of the features relative to one another disregarding another part of the features which are not to be displayed in the display diagram. Hence, it is possible that a part of the features is hidden, whereas another portion of the features remains unhidden. By taking this measure, some features may be disregarded for the display, for instance in accordance with user preferences. For instance, a user may hide specific features which are already identified so as to allow a clear display of the remaining features. Hence, the equidistant display or the display with at least a certain minimum distance between features may relate in this embodiment only to the unhidden features.

In an embodiment, the device further comprises a feature identification unit configured for identifying individual features in the measurement data by applying at least one feature identification criterion on the measurement data. Certain fractions of a fluidic sample to be separated are expected at certain retention times, so that the retention time, the intensity of the corresponding measurement peaks or other features can be used for fraction identification. Hence, such technical boundary conditions may be considered for the feature identification. Additionally, other feature identification parameters may be mathematic identification criteria such as the presence of a local maximum. The at least one feature identification criterion may be a degree of a match with preknown technical information, a degree of a match with an expected retention time of a feature, a degree of a match with an expected intensity of a feature, a degree of a match with an expected spectral shape of a feature, and/or a presence of a local extremum in the measurement data. However, other feature identification criteria may be applied as well.

In an embodiment, the device comprises a display unit configured for displaying the display diagram in accordance with the adjusted mode of displaying. Such a display unit may be configured for generating actual data to be displayed on a monitor or the like.

In an embodiment, the device is configured as a graphical user interface (GUI) which may be denoted as a user interface which allows people to interact with electronic devices such as computers or handheld devices. A GUI offers graphical icons and visual indicators as opposed to purely text based interfaces, typed command labels or text navigation to fully represent the information and actions available to a user. The actions may then be performed through direct manipulation of the graphical elements. Therefore, a user may input preferences to render the manipulated display appropriate for her or his purposes. For instance, one or more threshold parameters may be input by a user, therefore allowing to adjust the manipulation to the needs of a user. Alternatively, the system can be fully automatic.

In an embodiment, the measurement data comprises liquid or gaseous chromatography data. In one embodiment, the measurement data comprises coupled liquid chromatography and mass spectroscopy data. In an embodiment, the measurement data is provided by a measurement device which comprises at least one of a sensor device, a test device for testing a device under test or a substance, a device for chemical, biological and/or pharmaceutical analysis, a fluid separation system configured for separating compounds of a fluid, a capillary electrophoresis device, a liquid chromatography device, a gas chromatography device, an electronic measurement device, and a mass spectroscopy device. However, other applications and kinds of measurements are possible as well.

The device may be adapted for processing a displayed two-dimensional set of data, and particularly may be adapted for processing a measurement curve. Such a measurement curve may be provided by a measurement apparatus, for instance a life science apparatus or any other technical apparatus. Evaluating such measurement data may be conventionally a challenge and may be significantly simplified by the intuitive user interface according to an exemplary embodiment. However, in other embodiments, it is also possible to display three or more-dimensional data.

The measurement data may comprise liquid chromatography data. Such liquid chromatography data may be obtained by carrying out a sample separation procedure using a chromatographic column, wherein individual peaks may be detected optically and/or by a mass spectroscopy device. Exemplary embodiments may be applied to multi-dimensional sets of data of a liquid chromatography system, a gas chromatography system, particularly of a HPLC (high performance liquid chromatography). The system may offer specific functions related to the field of liquid chromatography data evaluation. For example, models for baselines of liquid chromatography data may be included in a database of the system as well as models of peaks, possible positions of peaks, possible line widths of peaks, etc.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

The illustrations in the drawings are schematic.

Figure 17:
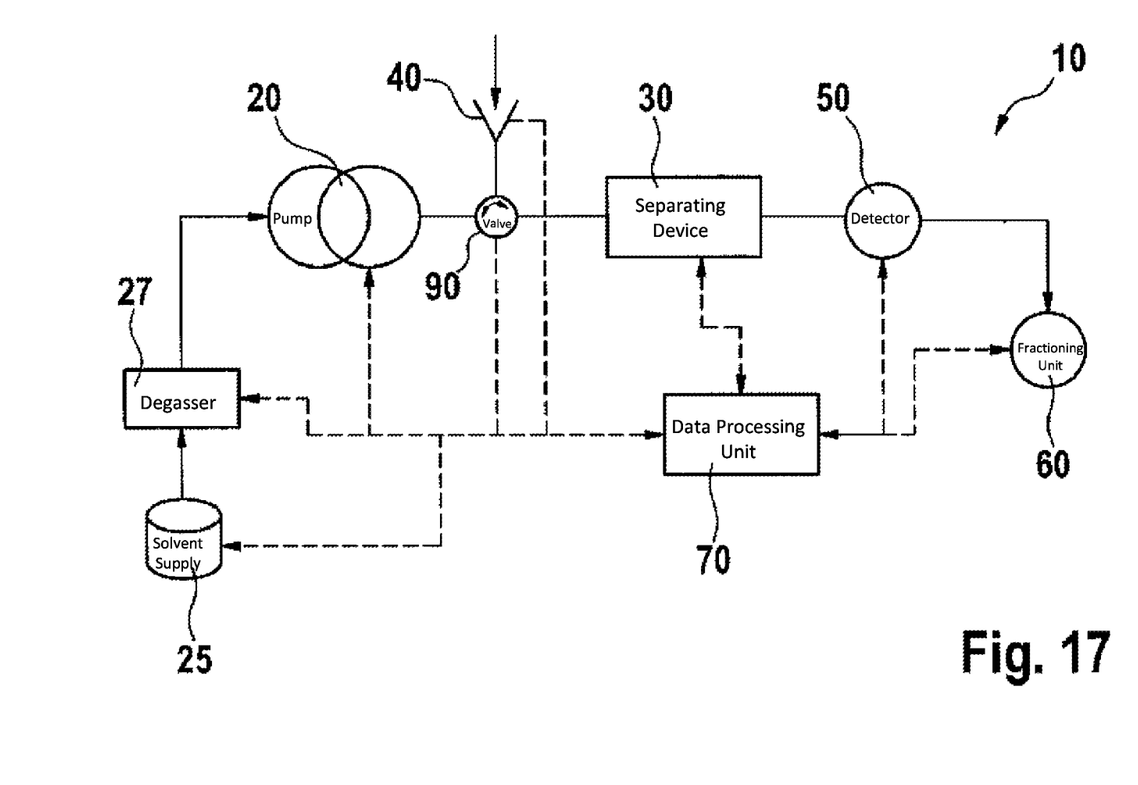
FIG. 17 shows a liquid separation system, in accordance with embodiments of the present invention, for instance used in high performance liquid chromatography (HPLC).

Referring now in greater detail to the drawings, FIG. 17 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 can be provided between the pump 20 and the separating device 30 in order to subject or add (often referred to as sample introduction) a fluidic sample into the mobile phase. The stationary phase of the separating device 30 is adapted for separating compounds of the fluidic sample. A detector 50 is provided for detecting separated compounds of the fluidic sample. A fractionating unit 60 can be provided for outputting separated compounds of the fluidic sample.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant over time, the so called isocratic mode, or varied over time, the so called gradient mode.

A data processing unit 70, which can be a PC or workstation, might be coupled (as indicated by the dotted arrows) to one or more of the devices in the liquid separation system 10 in order to receive information and/or control operation. For example, the data processing unit 70 might control operation of the pump 20 (for instance setting control parameters) and receive therefrom information regarding the actual working conditions (such as output pressure, flow rate, etc. at an outlet of the pump 20). The data processing unit 70 might also control operation of the solvent supply 25 (for instance setting the solvent/s or solvent mixture to be supplied) and/or the degas ser 27 (for instance setting control parameters such as vacuum level) and might receive therefrom information regarding the actual working conditions (such as solvent composition supplied over time, flow rate, vacuum level, etc.). The data processing unit 70 might further control operation of the sampling unit 40 (for instance controlling sample injection or synchronizing sample injection with operating conditions of the pump 20). The separating device 30 might also be controlled by the data processing unit 70 (for instance selecting a specific flow path or column, setting operation temperature, etc.), and send—in return—information (for instance operating conditions) to the data processing unit 70. Accordingly, the detector 50 might be controlled by the data processing unit 70 (for instance with respect to spectral or wavelength settings, setting time constants, start/stop data acquisition), and send information (for instance about the detected sample compounds) to the data processing unit 70. The data processing unit 70 might also control operation of the fractionating unit 60 (for instance in conjunction with data received from the detector 50) and provide data back.

Reference numeral 90 schematically illustrates a switchable valve which is controllable for selectively enabling or disabling specific fluidic paths within apparatus 10. The switchable valve 90 is not limited to the position between the pump 20 and the separating device 30 and can also be implemented at other positions, depending on the application.

The data processing unit 70 may also process and display measurement data (such as a chromatogram) measured by device 10 to enable a user to derive technical information from the measurement. Such procedures according to exemplary embodiments will be described in detail in the following description. Particularly, methods for evaluating chromatographic results using a manipulated display of a chromatogram will be explained.

In the following description, referring to FIG. 1, a device 100 for processing liquid chromatography data assigned to a liquid chromatography measurement on a fluidic sample to be separated will be explained.

The device 100 comprises a liquid chromatography apparatus 102 which may include components 20, 25, 27, 30, 40, 50, 60, 90 of device 10 of FIG. 17. The remaining components shown in FIG. 1 may be included in a data processing unit 70 shown in FIG. 17.

Measurement data obtained from a liquid chromatography experiment can be supplied from the liquid chromatography measurement device 102 to a peak identification unit 106. The peak identification unit 106 is configured for identifying individual peaks in the liquid chromatography data by applying certain feature identification criteria on the measured liquid chromatography data. For instance, the peak identification unit 106 may consider known technical information that specific peaks relating to different fractions of a fluidic sample are expected at certain retention times to identify individual peaks. Furthermore, the presence of a fraction in the fluidic sample usually results in a local extremum in the measurement signal. The result of the feature identification performed by the feature identification unit 106 may be stored in a database 104 which can also be accessed by the measurement device 102 and the further units shown in FIG. 1.

The identified positions (i.e. retention time values) of the individual features or peaks in the measurement data can then be supplied from the feature identification unit 106 to a feature position analysis unit 108. The feature position analysis unit 108 is configured for analyzing positions of the individual peaks relative to one another. Particularly, distances between peaks of each pair of adjacent peaks identified by the feature identification unit 106 may be determined by the feature position analysis unit 108. A result of the feature position analysis can be that some of the features are well separated so that they can be easily distinguishable by a user monitoring the measurement signal when plotted as such in a diagram. However, the feature position analysis may further yield the result that some features are too close together to be properly separable. Other adjacent features may have a very large distance so that the considerable gap between them does not transport relevant information. It may hence also happen that regions of the measurement signal are free of features so that the corresponding plotting region in a diagram is wasted.

In order to consider the results of the feature position analysis performed by the feature position analysis unit 108 for a subsequent display of the measurement data, the analyzed position and distance information may be supplied to a display adjustment unit 110. The display adjustment unit 110 is configured for adjusting, based on a result of the analyzing, a mode of displaying the identified features in a display diagram so that the identified features are more evenly distributed along a display axis as compared to a linear display of the features. It is also possible to consider for the adjustment of the display mode the boundary condition that adjacent features in the manipulated display have a distance exceeding a predefined threshold value from one another. More specifically, the display adjustment unit may adjust the mode of displaying in such a way that adjacent features of the measurement signal are positioned equidistantly along the display axis. Additionally or alternatively, the mode of displaying may be adjusted so that adjacent features are positioned to have a distance from one another which is larger than or equal to a predefined threshold value. The latter provision can prevent two features to be displayed in a way that they are overlapping to such an extent that they cannot be distinguished visually.

The adjustment of the mode of display may include compressing certain portions of the measurement signal along one axis and expanding other portions thereof along this axis. By taking this measure, the entire width of the display axis may be used for presenting an equalized peak distribution to a user. Correspondingly, a display density may vary along the display axis.

The data derived by the display adjustment unit 110 will be supplied to a display unit 112 which is configured for displaying the calculated display diagram in accordance with the adjusted mode of displaying. Hence, the display unit 112 may send displayable data to a user interface or input/output unit 116 which may be a graphical user interface. The latter may comprise output elements such as a monitor and input elements such as keys, buttons, a joystick, or a mouse. Via the input/output unit 116, a user may bidirectionally communicate with components 106, 108, 110, 112.

Figure 1:
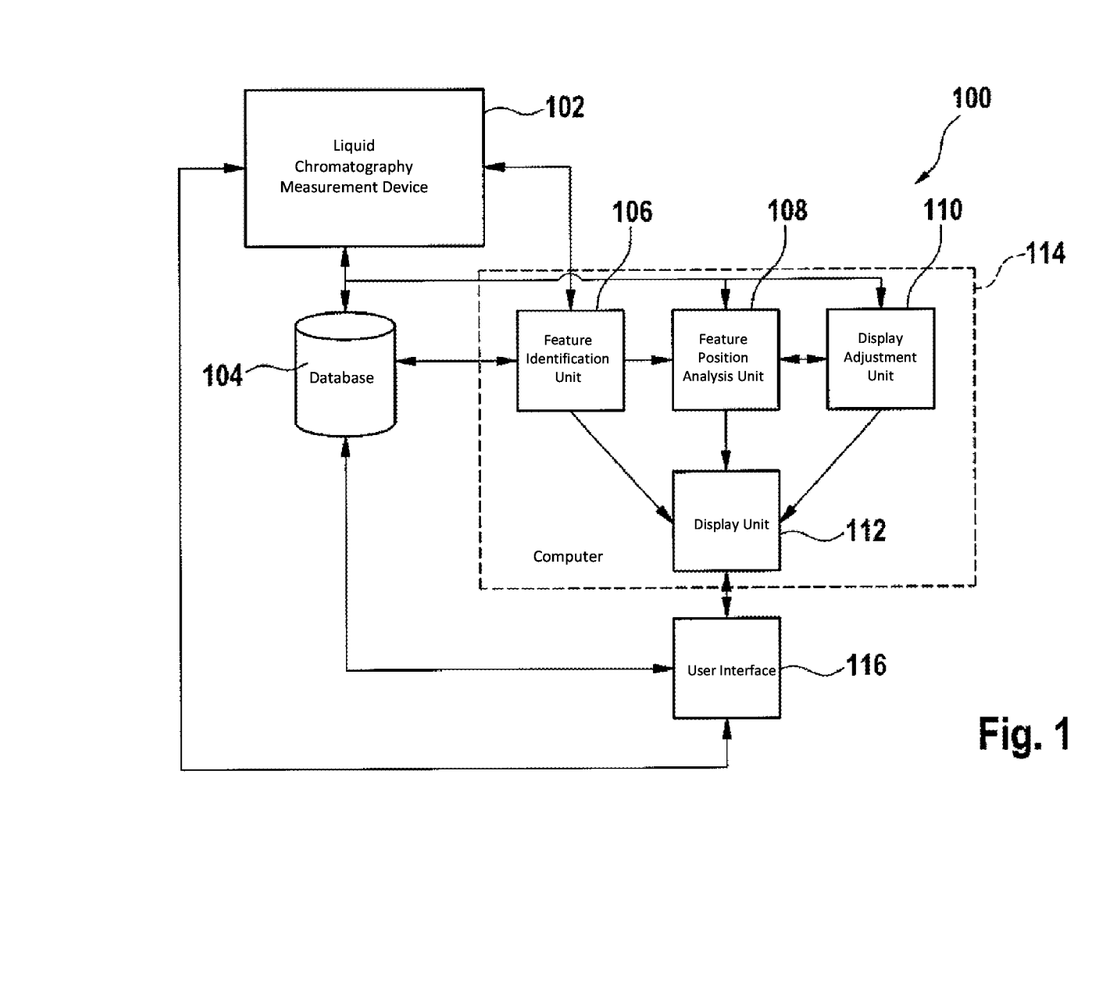
FIG. 1 illustrates a system for processing measurement data relating to a measurement on a fluidic sample to be separated according to an exemplary embodiment of the invention.

As can be taken from a dashed rectangle in FIG. 1 denoted with reference numeral 114, units 106, 108, 110, 112 can be realized as a common processor or computer. It is however also possible that each of the units 106, 108, 110, 112 is realized as a separate processor or computer or that some of the units 106, 108, 110, 112 are realized as a common processor.

In the following, referring to FIG. 2 to FIG. 6, a conventional way of displaying chromatographic measurement data will be illustrated for comparison purposes. Referring to FIG. 7 to FIG. 10, a corresponding way of displaying according to an exemplary embodiment of the invention will then be explained.

Figure 2:
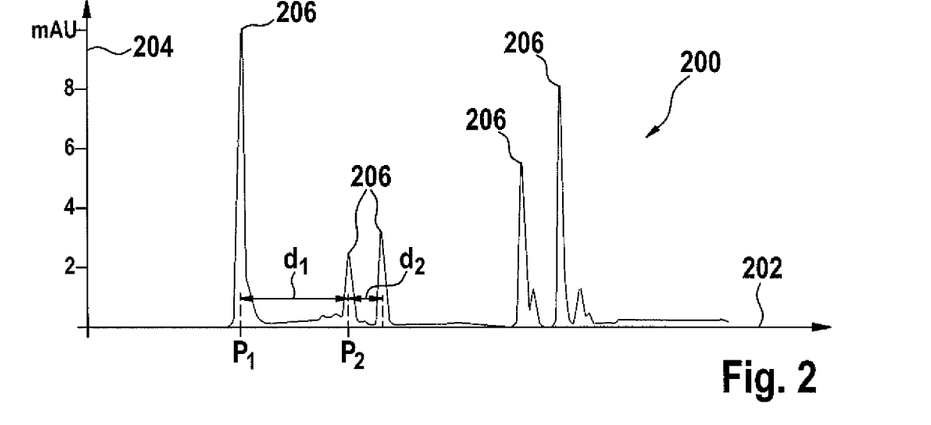
FIG. 2 illustrates a diagram showing a conventional representation of a chromatogram.

FIG. 2 shows a diagram 200 having an abscissa 202 along which a retention time of a chromatographic measurement signal is plotted, as known by those skilled in the art. Along an ordinate 204 an absorption intensity of the measurement signal is plotted in arbitrary units. As can be taken from FIG. 2, a number of peaks 206 as features of the measurement signal indicative of certain fractions of a fluidic sample are plotted. However, in FIG. 2, the distance between various peaks 206 is significantly different (for instance $d_1 \gg d_2$) so that some of the features are very close to one another and other features are far separated from one another. Hence, some of the peaks 206 can be hardly distinguished, whereas other portions of the measurement signal are almost free of information.

Figure 3:
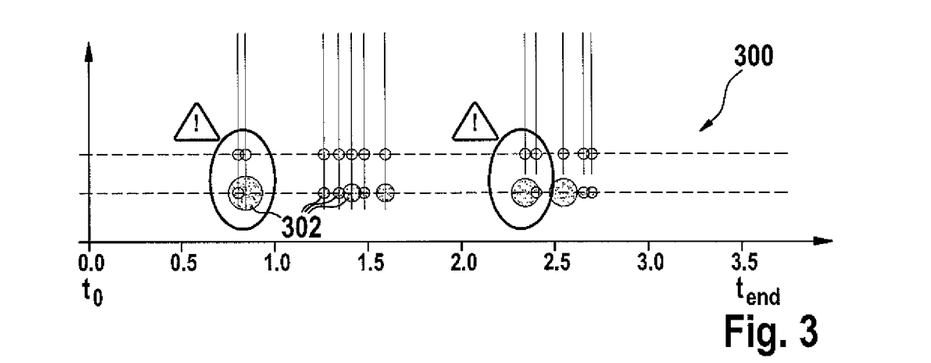
FIG. 3 shows a bubble plot in accordance with the diagram of FIG. 2.

FIG. 3 shows a bubble plot 300 in which the various peaks 206 are plotted as bubbles 302, i.e. as circular markers having a size which is indicative for the intensity of the respective peak 206. The distribution of the bubbles 302 along the retention time axis 202 is quite inhomogeneous so that there are clusters of bubbles 302 and regions without bubbles 302.

Figure 4:
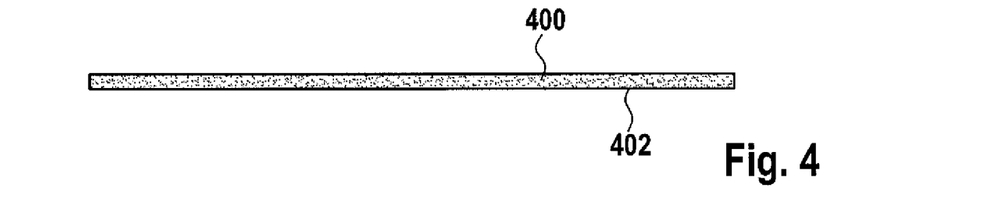
FIG. 4 shows a graphic indication of a constant time density for the diagrams of FIG. 2 and FIG. 3.

FIG. 4 illustrates the constant time density according to which the peaks 206 and bubbles 302 are plotted in FIG. 2 and FIG. 3, indicated by a bar 400 which has a constant color along the entire length. This indicates a constant density of the retention time plotted along the abscissa 202, i.e. a linear scaling. A diagram 500 in FIG. 5 again shows the dependency between the density function 506 along a plotting length 402 and a so-called retention time density 504, denoted as ptime.

Figure 5:
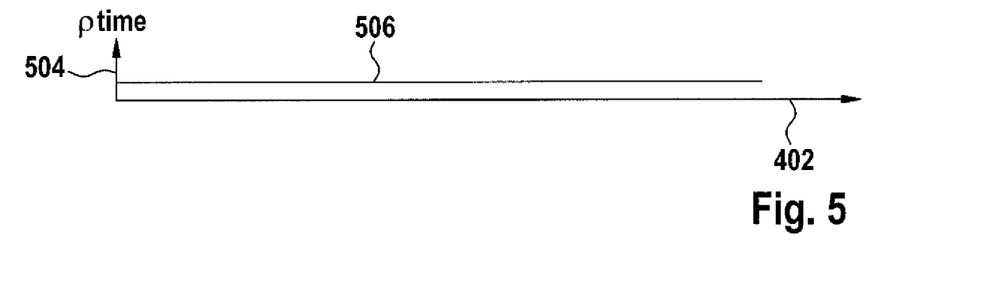
FIG. 5 shows a graph indicating the constant time density in accordance with FIG. 4.

Hence, individual chromatographic data are typically represented as a measured parameter representing a compound in the sample analyzed, for instance intensity of light absorbance, intensity of fluorescence, intensity of ionization. This parameter is typically plotted versus the retention time on a linear scale (FIG. 2). The time-density (time-intervals versus the plotting area) is constant (FIG. 4). To visualize chromatographic results, a projection of individual chromatograms or a series of chromatograms is used in FIG. 3 to simplify the data analysis by reducing the data amount. The peaks 206 are represented by the bubbles 302 or circles or other shapes with the center of gravity of that shape representing the retention time of that peak (FIG. 3). For a series of experiments, the individual experiments can be shown on one axis of a two dimensional representation and the retention time of the chromatograms is the second axis (horizontal in the shown examples). Further variations can be that the area of the shape represents the peak area or any other third parameter of the peak, for instance height, tailing factor, symmetry factor. Hence, FIG. 2 is a conventional display of chromatographic results in the form of a normal chromatogram, wherein projections of the chromatograms are shown in FIG. 3. The density of time-intervals across the display area is constant (linear time axis), as shown in FIG. 4 and FIG. 5.

Figure 6:
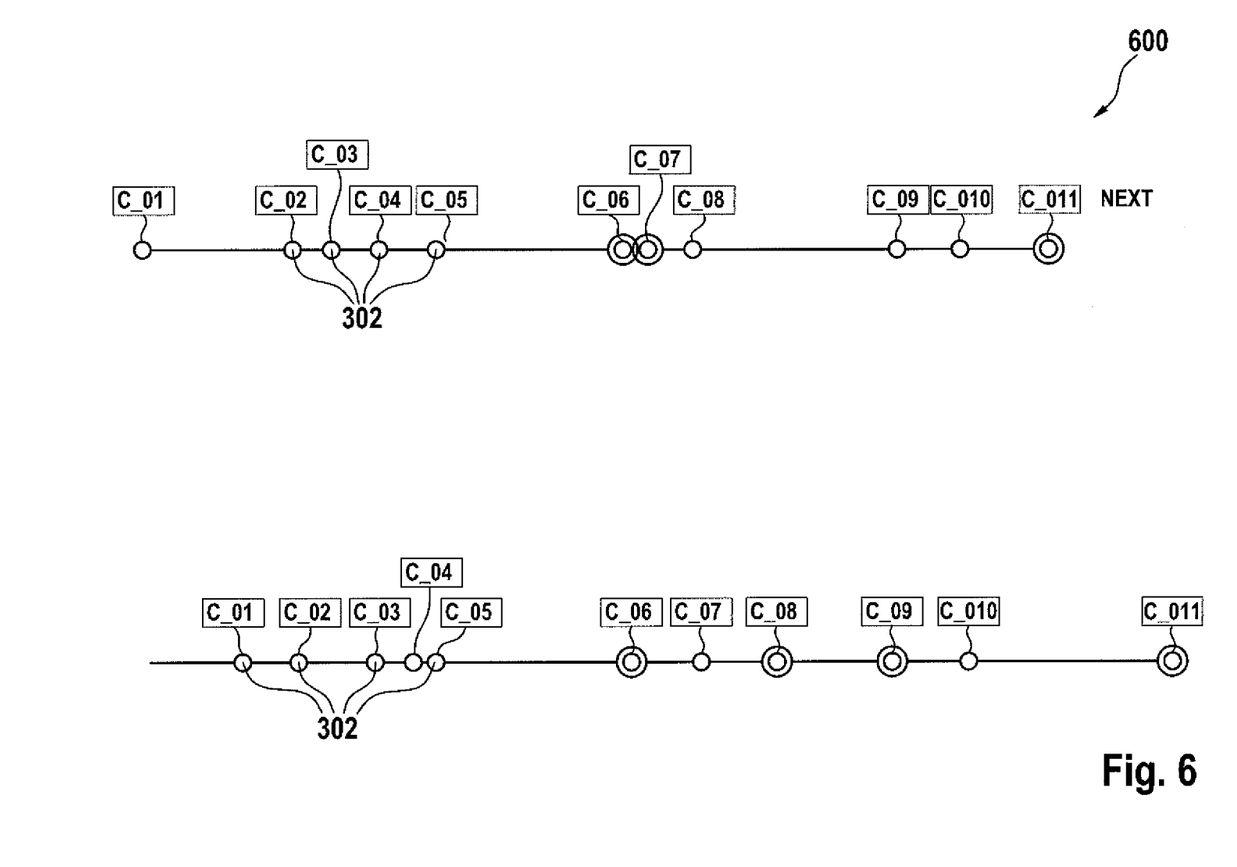
FIG. 6 shows a projection display in accordance with a conventional chromatogram.

FIG. 6 shows a plot 600 indicating the various peaks 206 in form of bubbles 302 in a projection.

In contrast to the conventional approaches of FIG. 2 to FIG. 6, exemplary embodiments allow for an equidistant chromatographic peak display, as will be explained in the following.

In an embodiment, it is possible to distribute all found peaks equally over the length of the time axis. This can be done either directly on the chromatogram level (see FIG. 7) or with the projection of a chromatogram (see FIG. 8). The time-axis will not be linear but can be polynomial (see FIG. 9 and FIG. 10). FIG. 7 to FIG. 10 show an equidistant peak display using a non-linear time axis, whereby closely eluting peaks are immediately visible, even if they have a big difference in compound concentrations. The distribution of the peaks can be done either between the start and end-time of the analytical run as boundaries or between the first and last identified peaks. This will separate all identified peaks in a proper way and makes efficient use of the display area, since no display area is wasted for empty regions of the chromatogram. This will now be described in more detail.

Figure 7:
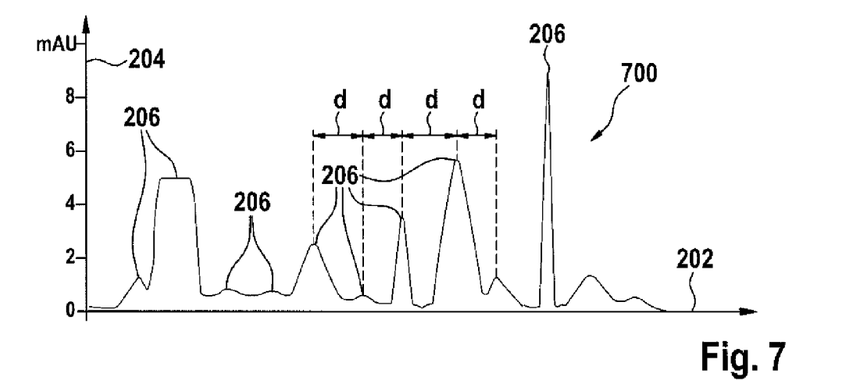
FIG. 7 shows a diagram with an equidistant display of peaks of a chromatogram according to an exemplary embodiment of the invention.

FIG. 7 shows a display diagram 700 displaying the measurement data of FIG. 2 according to an exemplary embodiment of the invention.

Again, the retention time axis 202 is plotted together with absorption intensity axis 204. However, in the diagram 700, a physical plotting distance, d, between each two adjacent peaks 206 is identical over the entire extension of the retention time axis 202 so that all displayed peaks 206 are arranged in an equidistant pattern.

As can be taken from FIG. 7, each peak 206 represents a combination of a value of the retention time as a first measurement parameter with a value of the absorption intensity as a second measurement parameter. The display diagram 700 is a coordinate system having the retention time axis 202 along which the value of the retention time parameter is displayed for the peaks 206 in a non-linear manner in accordance with the adjusted mode of displaying. The second display axis 204 displays the value of the absorption intensity as second measurement parameter for the peaks 206 in a linear mode of displaying.

Figure 8:
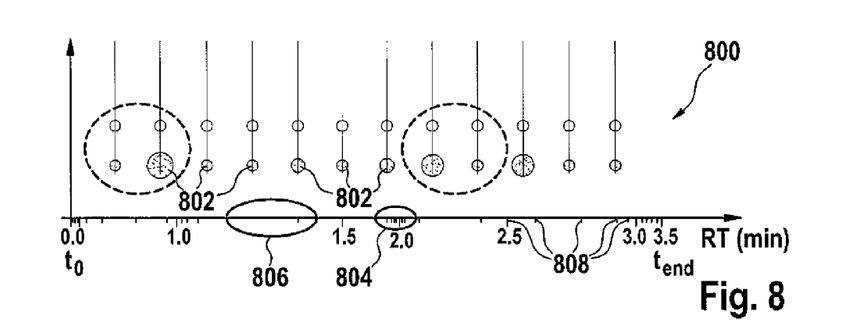
FIG. 8 illustrates a bubble plot with equidistantly displayed peaks in accordance with the diagram of FIG. 7.

Bubble diagram 800 shown in FIG. 8 is another way of displaying the measurement data according to an embodiment of the invention. According to FIG. 8, each peak 206 represents a combination of a value of the retention time as the first measurement parameter with the value of the absorption intensity as the second measurement parameter. Although (like the display diagram 700 and its first display axis 202) the bubble diagram 800 has as the first display axis the retention time axis RT, the value of the absorption intensity is not displayed along the vertical coordinate axis but in contrast to this encoded by the bubbles 802 as a graphical marker. Therefore, it is not necessary to use the vertical coordination coordinate axis for displaying the intensity which is encoded by the area of the respective bubble 802.

Figure 9:
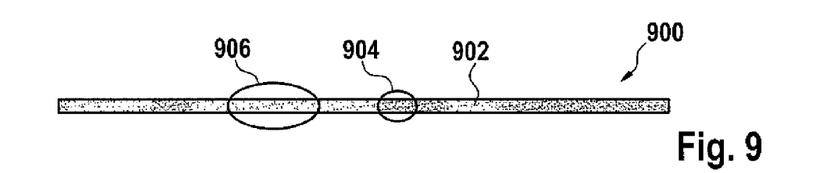
FIG. 9 shows a bar visually illustrating a density function indicative of a plotted density of the retention time in the diagrams of FIG. 7 and FIG. 8.

As can be taken from a density plot 900 shown in FIG. 9, the varying retention time density as plotted along the retention time axis is plotted in the form of a color encoded display of the density function. For instance, a first region 804 represents a zone in which the retention time axis 202 is heavily compressed. Accordingly, the color of the respective portion 904 in FIG. 9 is dark grey. In contrast to this, another portion 806 along the retention time axis show a relatively high density of features 206 so that an expanded portion of the retention time axis is plotted here. Accordingly, the color of the color bar 900 is light grey in the region 806, as indicated by reference numeral 906. In FIG. 8, the display of the density function is realized as scaling markers 808 arranged with varying distance from one another (i.e. non-equidistantly) along the retention time axis 202.

A user analyzing the features 206 in the equidistant plot of FIG. 7 or FIG. 8 may simply look either at the scaling markers 808 or on the color code bar 900 in order to get an impression regarding which portions along the retention time axis 202 are compressed and which portions are expanded. Hence, a convenient equidistant display may be combined with the advantage of the full scaling information derivable from the retention time density plots.

Figure 10:
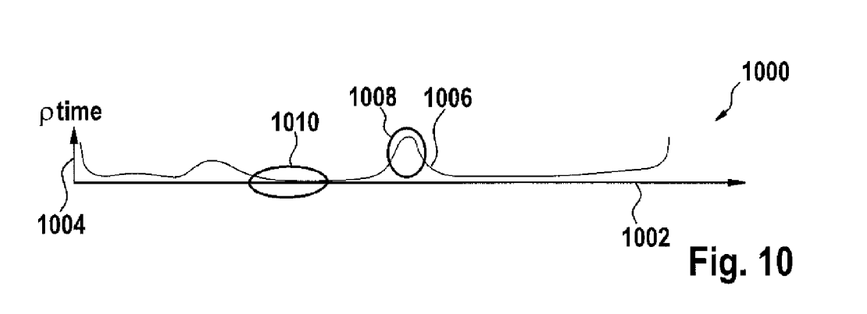
FIG. 10 shows a graph illustrating the density function of FIG. 9.

The manipulation along the retention time axis 202 may also be derived from FIG. 10, in which a diagram 1000 is shown having an abscissa 1002 along which the plotting length is plotted. The time density ptime is plotted along an ordinate 1004. As can be taken from curve 1006, regions of high compression (compare reference numeral 1008) can be clearly distinguished from regions with a low compression or even expansion (compare reference numeral 1010).

Figure 11:
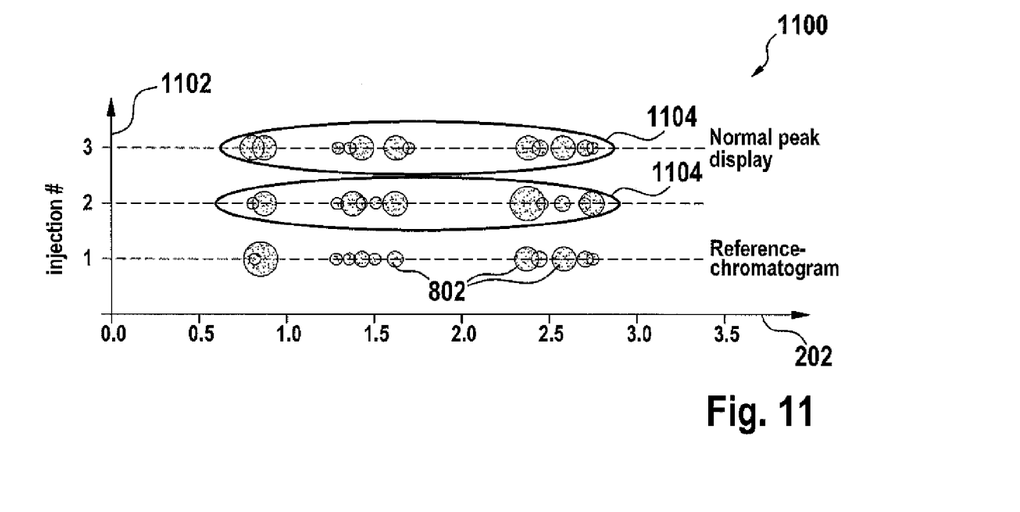
FIG. 11 shows a conventional bubble plot simultaneously displaying multiple data sets relating to different measurements using a linear retention time axis.
Figure 12:
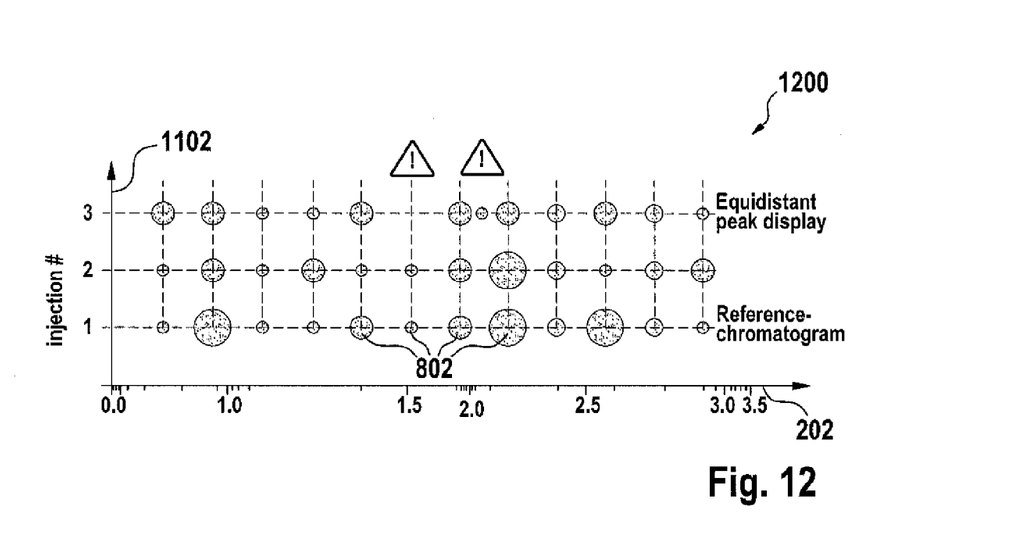
FIG. 12 shows the same information as FIG. 11 in a display mode according to an exemplary embodiment of the invention with a manipulated retention time axis.

An advantage of embodiments lies in the two dimensional representation using a projection of the chromatograms in a series of chromatograms from related samples using one sample as reference, for example from quality control analysis. Missing or additional peaks are immediately visible as "holes" or off-center peaks in the highly regular gridline of experiments versus peaks (see FIG. 11 to FIG. 14). FIG. 11 and FIG. 12 show a normal and an equidistant peak display in a series of experiments using projections of the chromatograms. In FIG. 12, missing or additional compounds/peaks compared to a reference chromatogram that determines the time-axis are immediately visible, even with much larger data sets. This will now be described in more detail.

FIG. 11 shows a diagram 1100 illustrating a conventional chromatogram in the form of a bubble plot. Again, the abscissa 202 shows the retention time plotted on a linear scale, whereas individual injections or measurements of different but comparable samples are plotted along an ordinate 1102. The individual bubbles represent the various fractions of the fluidic sample. Each data set 1104 corresponds to a respective measurement so that in the diagram of FIG. 11 three measurements or injections and therefore three data sets 1104 are plotted. One of the data sets 1104 corresponds to a reference chromatogram.

FIG. 12 shows a diagram 1200 illustrating the same data as plotted in FIG. 11 in a plot according to an exemplary embodiment of the invention. As can be taken from FIG. 12, the retention time axis 202 is now manipulated, i.e. is compressed in certain portions and is expanded in other portions. The injection axis 1102 is plotted in the same linear style as in FIG. 11. Now, all the bubbles 802 of a data set 1104 are distributed equidistantly along the horizontal axis in the diagram 1200.

Figure 13:
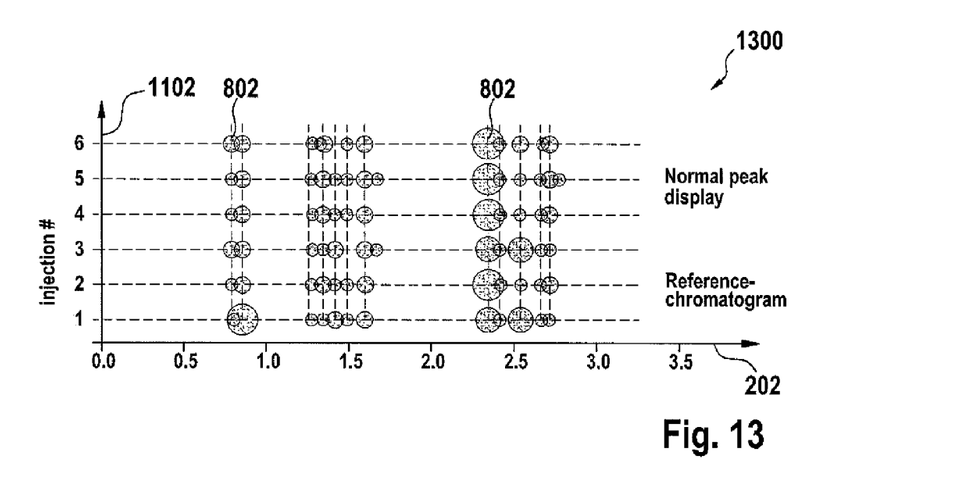
FIG. 13 shows a conventional bubble plot simultaneously displaying multiple data sets relating to different measurements using a linear retention time axis.
Figure 14:
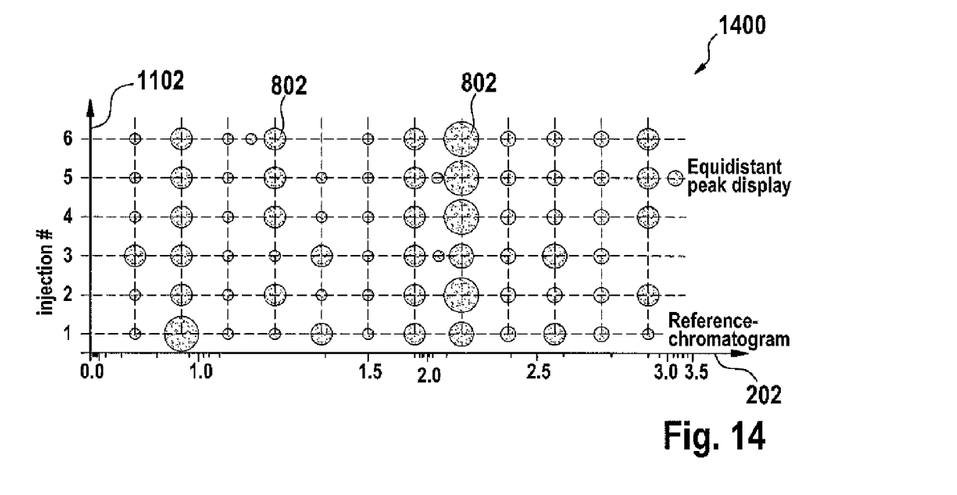
FIG. 14 shows the same information as FIG. 13 in a display mode according to an exemplary embodiment of the invention with a manipulated retention time axis.

In a same way, a conventional diagram 1300 shown in FIG. 13 can be displayed more efficiently in the form of diagram 1400 shown in FIG. 14 and illustrating a plot according to an exemplary embodiment of the invention with an equidistant arrangement of the bubbles 802.

Figure 15:
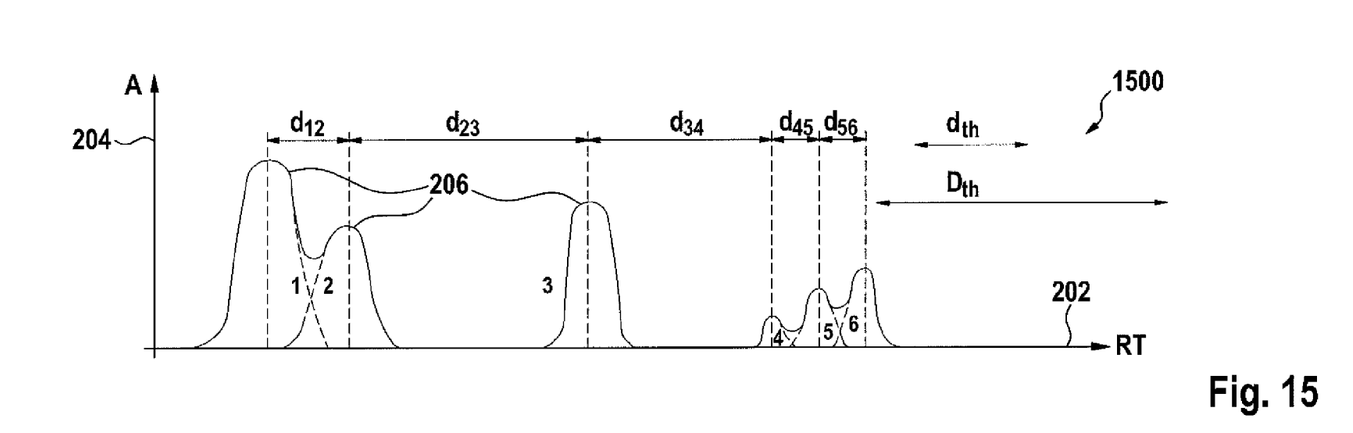
FIG. 15 illustrates a diagram showing a conventional representation of a chromatogram with overlapping peaks.

FIG. 15 illustrates a diagram 1500 showing a conventional representation of a chromatogram, similar as in FIG. 2. Six peaks 206 are indicated with the numbers 1, 2, 3, 4, 5, and 6. The respective distances $d_{12}$, $d_{23}$, $d_{34}$, $d_{45}$, and $d_{56}$ between each pair of adjacent peaks 206 is shown as well. While some adjacent peaks 206 (2-3, 3-4) are well separated from one another, other adjacent peaks 206 (1-2, 4-5, 6-6) are so close together that they overlap and are difficult to be interpreted separately. The latter pairs of peaks 206 have distances $d_{12}$, $d_{45}$, and $d_{56}$ from one another being smaller than a predefined threshold value $d_{th}$. The former pairs of peaks 206 have distances $d_{23}$ and $d_{34}$ from one another being larger than the threshold value $d_{th}$.

Figure 16:
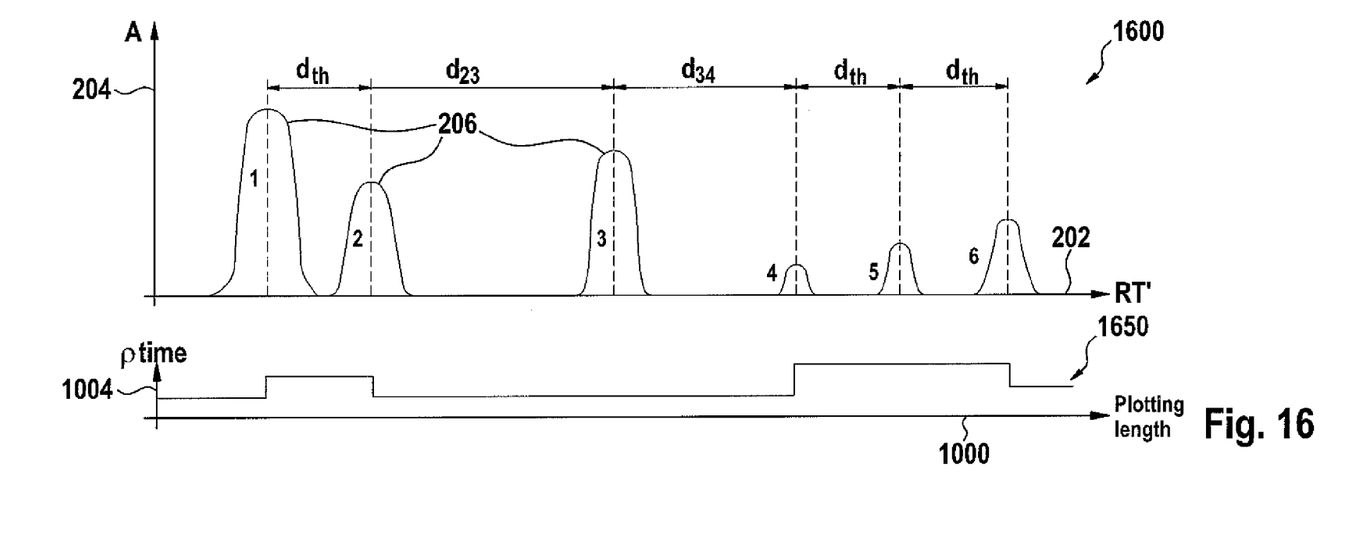
FIG. 16 shows a diagram according to an exemplary embodiment of the invention illustrating the same measurement data as FIG. 15 with a display of the peaks having at least a predetermined distance from one another so as to be separated.

FIG. 16 shows a diagram 1600 according to an exemplary embodiment of the invention illustrating the same measurement data as FIG. 15 with a display of all peaks 206 having at least the predetermined distance $d_{th}$ from one another. In the diagram 1600, all peaks 206 originally having distances $d_{12}$, $d_{45}$, and $d_{56}$ from one another being smaller than the threshold value $d_{th}$ are plotted at a distance $d_{th}$ from one another. All peaks 206 originally having distances $d_{23}$ and $d_{34}$ from one another being larger than the threshold value $d_{th}$ are plotted so as to be spaced by their original distances $d_{23}$ and $d_{34}$. This corresponds to a manipulation of the time density which can be taken from diagram 1650.

The display according to FIG. 16 is further adjusted so that adjacent features 206 are positioned to have a distance from one another which is always below a further predefined threshold value $D_{th}$ shown in FIG. 15. In the present case, none of the distances $d_{12}$, $d_{23}$, $d_{34}$, $d_{45}$, and $d_{56}$ exceeds $D_{th}$ so that a corresponding compressing is not necessary according to the shown embodiment. Should however a pair of adjacent features 206 have a distance which exceeds $D_{th}$, their display can be optionally manipulated so that they are displayed at the maximum approved distance $D_{th}$ from one another. By taking this measure, it may be prevented that a quite large portion of the displayed region does not show meaningful information. Compressing such a portion of the display may allow to use the display area even more efficiently.

In conventional modes to display chromatographic results overlapping peaks are difficult to identify. Changes between different samples of a series are difficult to identify especially if the chromatogram is very crowded in certain regions, like for peptide maps or natural product analysis. An equidistant chromatographic peak display according to an embodiment of the invention makes it very easy to see changes in series of experiments of related samples.

In an embodiment, a method in accordance with the following procedure may be performed:
1. Acquire chromatogram as measured parameter versus retention time
2. Integrate chromatogram to define peaks based on user defined integration parameters
3. Define retention time of peak as maximum of peak height
4. Build list of all peaks based on peak retention time
5. Define function that converts time-value of each chromatographic data-point to an x-position such that the x-positions of the peak-maxima are equidistant.
6. Build table of all measured parameter (for instance intensity) as y-position versus new x-position (this is a coordinate system transformation)
7. Draw chromatogram
7a. As measured parameter versus time plot by plotting all points defined in 6 and connecting all points
7b. As projection of the chromatogram by plotting a shape with its center of gravity at the x-position based on 5 for each identified peak, the shapes might vary in size depending on any third parameter.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A device for processing measurement data assigned to a measurement on a fluidic sample to be separated by a fluid separation apparatus, the measurement data comprising a plurality of features indicative of different fractions of the fluidic sample, the device comprising:
a computer configured for receiving the measurement data from the fluid separation apparatus, the computer comprising one or more processors and one or more memories, the one or more processors comprising:
a feature position analysis unit configured for analyzing positions ($p_1$, $p_2$, $d_1$, $d_2$) of at least a part of the features of the received measurement data relative to one another, the part of the features comprising two or more pairs of adjacent features having measured separation distances $d_1$, $d_2$; and
a display adjustment unit configured for adjusting, based on a result of the analyzing, a mode of displaying the part of the features along at least one display axis of a display diagram so that the at least one display axis is non-linearly scaled whereby a spacing between units of the at least one display axis varies and the spacing is scaled to be different in different portions of the at least one display axis, and so that
the adjacent features of the two or more pairs of adjacent features are positioned to have a plotting distance (d) from one another which is larger than or equal to a predefined threshold value ($d_{th}$), and
a first plotting distance between a first pair of the adjacent features and a second plotting distance between a second pair of adjacent features have each been differently scaled in the different portions; and
a display unit configured for receiving a result of the adjusting and for displaying the part of the features and the display diagram in accordance with the mode of displaying adjusted by the display adjustment unit, wherein the at least one display axis is selected from the group consisting of: a chromatographic retention time axis, a chromatographic retention volume axis, and a mass-to-charge ratio axis.

2. The device of claim 1, wherein the display adjustment unit is configured for adjusting the mode of displaying so that all features are located equidistantly along the at least one display axis or all adjacent features are positioned to have said plotting distance (d) from one another which is larger than or equal to the predefined threshold value ($d_{th}$).

3. The device of claim 1, wherein the display adjustment unit has a configuration selected from the group consisting of:
the display adjustment unit is configured for adjusting the mode of displaying so that a display of a part of the features is compressed along a corresponding portion of the at least one display axis;
the display adjustment unit is configured for adjusting the mode of displaying so that a display of another part of the features is expanded along a corresponding other portion of the at least one display axis; and
both of the foregoing.

4. The device of claim 1, wherein the display adjustment unit is configured for adjusting the mode of displaying so that the adjacent features of the two or more pairs of adjacent features are positioned to have said plotting distance (d) from one another which is larger than or equal to a predefined threshold value ($d_{th}$), and are positioned to have said plotting distance (d) from one another which is below a further predefined threshold value ($D_{th}$).

5. The device of claim 1, wherein the display adjustment unit is configured for determining a density function to be displayed along the at least one display axis indicative of a varying density according to which a parameter is displayed along the at least one display axis in the mode of displaying adjusted by the display adjustment unit.

6. The device of claim 5, wherein a display of the density function comprises at least one of the group consisting of a color encoded display of the density function, a display of the density function in terms of scaling markers arranged along the at least one display axis, and a density function coordinate system displaying a curve indicative of the density function.

7. The device of claim 1, wherein the mode of displaying adjusted by the display adjustment unit is a mode of displaying at least the part of the features in accordance with a polynomial density function along the at least one display axis of the display diagram.

8. The device of claim 1, wherein the mode of displaying adjusted by the display adjustment unit is a mode of displaying at least the part of the features exclusively an excerpt of the measurement data between a first identified feature and a last identified feature.

9. The device of claim 1, wherein each feature represents a combination of a value of a first measurement parameter with a value of a second measurement parameter, wherein the display diagram is a coordinate system having a first display axis along which the value of the first measurement parameter is displayable for at least a part of the features in accordance with the mode of displaying adjusted by the display adjustment unit, and having a second display axis along which the value of the second measurement parameter is displayable for at least a part of the features.

10. The device of claim 1, wherein each feature represents a combination of a value of a first measurement parameter with a value of a second measurement parameter, wherein the display diagram is a coordinate system having a first display axis along which the value of the first measurement parameter is displayable for at least a part of the features in accordance with the mode of displaying adjusted by the display adjustment unit, wherein the value of the second measurement parameter is displayable for at least a part of the features encoded by a graphical property of a respective marker in the coordinate system.

11. The device of claim 10, wherein the graphical property is a size of the marker.

12. The device of claim 10, wherein the measurement data has a plurality of data sets, each data set being assigned to a respective one of a plurality of measurements, each data set having multiple features being indicative of different fractions of a fluidic sample, wherein the display diagram has a second display axis along which at least a part of the data sets is displayable for at least a part of the features.

13. The device of claim 9, wherein the second measurement parameter is indicative of a detection intensity of a peak of a chromatography measurement.

14. The device of claim 1, wherein the feature position analysis unit is configured for analyzing the measured separation distances $d_1$, $d_2$ between at least a part of adjacent features.

15. The device of claim 1, wherein the feature position analysis unit is configured for analyzing positions ($p_1$, $p_2$, $d_1$, $d_2$) of only a part of the features relative to one another disregarding another part of the features which are not to be displayed in the display diagram.

16. The device of claim 1, comprising a feature identification unit configured for identifying individual features in the measurement data by applying at least one feature identification criterion on the measurement data.

17. The device of claim 16, wherein the at least one feature identification criterion comprises at least one of a degree of a match with preknown technical information, a degree of a match with an expected retention time of a feature, a degree of a match with an expected intensity of a feature, a degree of a match with an expected spectral shape of a feature, and a presence of a local extremum in the measurement data.

18. A method of processing measurement data assigned to a measurement on a fluidic sample to be separated by a fluid separation apparatus, the measurement data comprising a plurality of features indicative of different fractions of the fluidic sample, the method comprising:
receiving, at a processor, the measurement data from the fluid separation apparatus;
analyzing, with the processor, positions ($p_1$, $p_2$, $d_1$, $d_2$) of at least a part of the features of the received measurement data relative to one another, the part of the features comprising two or more pairs of adjacent features having measured separation distances $p_1$, $p_2$;
adjusting, with the processor, based on a result of the analyzing, a mode of displaying the part of the features along at least one display axis of a display diagram so that the at least one display axis is non-linearly scaled whereby a spacing between units of the at least one display axis varies and the spacing is scaled to be different in different portions of the at least one display axis, and so that the adjacent features of the two or more pairs of adjacent features are positioned to have a plotting distance (d) from one another which is larger than or equal to a predefined threshold value ($d_{th}$), and a first plotting distance between a first pair of the adjacent features and a second plotting distance between a second pair of adjacent features have each been differently scaled in the different portions;

receiving, at a display unit, a result of the adjusting; and displaying, with the display unit, the part of the features and the display diagram in accordance with the mode of displaying adjusted by the display adjustment unit, wherein the at least one display axis is selected from the group consisting of: a chromatographic retention time axis, a chromatographic retention volume axis, and a mass-to-charge ratio axis.

19. The device of claim 1, wherein the display adjustment unit is configured for adjusting, based on a result of the analyzing, the mode of displaying the part of the features along at least one display axis of a display diagram so that the adjacent features of the two or more pairs of adjacent features are positioned equidistantly along the at least one display axis.

* * * * *